United States Patent [19]

Duchek

[11] Patent Number: 5,227,526
[45] Date of Patent: Jul. 13, 1993

[54] RESOLUTION OF 3-DIMETHYLAMINO-2-METHYLPROPIOPHENONE (3-DAMP)

[75] Inventor: John R. Duchek, St. Louis, Mo.

[73] Assignee: Mallinckrodt Specialty Chemicals Company, Chesterfield, Mo.

[21] Appl. No.: 899,291

[22] Filed: Jun. 16, 1992

[51] Int. Cl.$^5$ .......................................... C07C 221/00
[52] U.S. Cl. .................................................. 564/304
[58] Field of Search .................................... 564/304

[56] References Cited

U.S. PATENT DOCUMENTS

| | | | |
|---|---|---|---|
| 2,804,865 | 8/1957 | L'Italien et al. | 564/304 |
| 3,312,733 | 4/1967 | Howe | 564/304 |
| 4,370,500 | 1/1983 | Kurose | 564/304 |
| 4,968,837 | 11/1990 | Manimaran et al. | 564/304 |

FOREIGN PATENT DOCUMENTS

| | | | |
|---|---|---|---|
| 173204 | 9/1978 | Hungary | 564/304 |
| 2-1429 | 1/1990 | Japan | 564/304 |

OTHER PUBLICATIONS

Berrang et al, J. Org. Chem., vol. 47, pp. 2643–2647 (1982).

*Primary Examiner*—James H. Reamer
*Attorney, Agent, or Firm*—Rothwell, Figg, Ernst & Kurz

[57] ABSTRACT

In a process for resolving 3-dimethylamino-2-methylpropiophenone (3-DAMP) material, a methanol solution containing a mixture of both l- and d-enantiomers of 3-DAMP is formed. To this solution, ditoluyl-(L)-tartaric acid or ditoluyl-(D)-tartaric acid is added, so as to precipitate either the l- or d-enantiomer of 3-DAMP as a salt. The precipitate then is isolated as a salt of a substantially pure enantiomer of 3-DAMP.

18 Claims, No Drawings

RESOLUTION OF 3-DIMETHYLAMINO-2-METHYLPROPIOPHE-NONE (3-DAMP)

BACKGROUND OF THE INVENTION

1. Field of the Invention

The present invention relates generally to resolving 3-DAMP enantiomers.

2. Description of the Background Art

The compound d-oxyphene is an intermediate in the synthesis of α- d-propoxyphene, a narcotic which is recognized and accepted as possessing effective analgesic qualities in humans.

A typical prior art procedure for producing d-oxyphene starts with propiophenone, which is reacted with dimethylamine hydrochloride and formaldehyde to produce racemic 3-DAMP. The racemic 3-DAMP is treated with benzyl Grignard reagent to produce a second asymmetric center. This results in the production and α- and β-oxyphene, which are produced as a diastereomeric pair of racemic mixtures with α-oxyphene as the major product. The desired α-oxyphene isomer then is resolved using traditional crystallization methods to remove the unwanted enantiomer and the β-diastereomer using a resolving agent such as D-10-camphorsulfonic acid, since the α-oxyphene enantiomer cannot be used to make the narcotic α-d-propoxyphene analgesic. While β-oxyphene can be used to produce the antitussive levopropoxyphene (α-1-propoxyphene), this is a minor product in comparison with α-d-propoxyphene.

Hungarian Patent Publication No. 173,204 (Jeno Korsi et al.) describes resolution of dl-3-DAMP using (+)-dibenzoyl-D-tartaric acid in acetone at 55° C. to obtain the desired 1-3-DAMP for the production of α-d-oxyphene. In the initial reaction, less than half of the 3-DAMP is resolved from the acetone mother liquor solution. The mother liquor then is heated so as to remove half the volume, which racemizes the 3-DAMP part of the salt so as to resolve an additional small yield of less than 10% of the original 3-DAMP starting material. This is done a total of four times to obtain approximately 95% of the 3-DAMP starting material with an optical rotation of $[\alpha]^{25}_D = +50°-60°$ and a melting point of 113°-134° C. (water content variable).

There are several major drawbacks of the procedure described in the Hungarian patent. First of all, very dilute conditions are necessary to allow resolution of only relatively small amounts of the desired enantiomer in large quantities of acetone. The procedure requires repeated boil downs to obtain the ultimate yield, and impurities tend to build up in the mother liquor during the boil-downs. Furthermore, from the rotation and melting point data, it is evident that resolution is not complete.

There remains a need in the art for improved methods for resolving 3-DAMP.

SUMMARY OF THE INVENTION

In accordance with the present invention, a process for resolving 3-dimethylamino-2-methylpropiophenone (3-DAMP) material, comprises forming a methanol solution containing a mixture of both 1- and d-enantiomers of 3-DAMP. To this methanol solution is added only one acid selected from a group consisting of ditoluyl-(L)-tartaric acid and ditoluyl-(D)-tartaric acid, so as to precipitate one of said enantiomers as a salt. The precipitate then is isolated as a salt of a substantially pure enantiomer of 3-DAMP.

DETAILED DESCRIPTION OF THE PREFERRED EMBODIMENTS

Applicant has surprisingly discovered that ditoluyl-(L)-tartaric acid can be utilized to resolve 1-3-DAMP in methanol. In contrast with the above-described Hungarian method which utilizes (+)-dibenzoyl-D-tartaric acid to resolve 1-3-DAMP, it is the opposite enantiomer of ditoluyl tartaric acid (L instead of D) which resolves 1-3-DAMP in accordance with the present invention.

Furthermore, no resolution is accomplished when utilizing the inventive ditoluyl-(L)-tartaric acid in prior art dilute acetone.

Additionally, attempts to utilize prior art dibenzoyl-(D)-tartaric acid in the inventive methanol solution at the concentrations described below have resulted in an unfilterable hard solid in which the methanol cannot be seen or removed.

As indicated above, when ditoluyl-(L)-tartaric acid in methanol is utilized to resolve dl-3-DAMP, a substantially pure salt of the 1-3-DAMP enantiomer is resolved. The d-3-DAMP enantiomer can be obtained by substituting ditoluyl-(D)-tartaric acid in the same manner.

In preferred embodiments, a racemic mixture of dl-3-DAMP is dissolved in methanol, and an equimolar amount of the desired ditoluyltartaric acid, e.g., ditoluyl-(L)-tartaric acid, is added to the solution, resulting in precipitation of the desired 3-DAMP enantiomer. The 3-DAMP material remaining in solution will then interconvert, and the desired 3-DAMP enantiomer salt precipitates as it is formed. Stirring facilitates interconversion and subsequent precipitation of the desired enantiomer salt. At room temperature, interconversion and precipitation of most of the desired 3-DAMP enantiomer salt requires 6–10 days to go to completion, while at 40° C. it requires a mere 30–35 hours. At higher temperatures, the resolution proceeds faster but is accompanied by some decomposition which gives lower yields. According to this procedure, about 85–90% of the original dl-3-DAMP can be isolated as the desired 3-DAMP enantiomer salt, for example, 1-3-DAMP ditoluyl-(L)-hydrogen tartrate.

After isolation of the desired enantiomer precipitate from the mother liquor, the methanol solution can be recycled by further adding to the solution a dl-3-DAMP mixture and the appropriate ditoluyltartaric acid. Mother liquor has been recycled in this manner up to seven times with no adverse effects.

The precipitate isolated from the mother liquor can be converted to the free amine of the desired substantially pure enantiomer of 3-DAMP without substantial loss of optical purity. For example, when the isolated precipitate is the salt of 1-3-DAMP, such is converted to the free amine by first forming an aqueous solution of the 1-3-DAMP salt.

In preferred embodiments, the aqueous solution of the 1-3-DAMP salt is formed at a pH of about 9 or higher, more preferably within the range of from about pH 10.5 to about pH 11, and most preferably at a pH of about 10.8.

After formation of the aqueous solution of the 1-3-DAMP salt, 1-3-DAMP is extracted from the aqueous solution with an aprotic solvent. In particularly preferred embodiments, the 1-3-DAMP is extracted from the aqueous solution at a temperature within the range of from about 0° C. to about 10° C., most preferably at a temperature of between about 0° C. and about 5° C.

The aprotic solvent can be any suitable solvent in which the desired 3-DAMP enantiomer is soluble, for example, methylene chloride, hexane, t-butylmethyl ether, and the like. In preferred embodiments, methylene chloride is utilized as the aprotic solvent for extraction of 1-3-DAMP. After extraction, the aprotic solvent can be separated from the desired 3-DAMP enantiomer by any suitable method, such as by evaporation of the aprotic solvent.

The invention is further illustrated by the following examples, which are not intended to be limiting.

EXAMPLE I

Resolution of 1-3-DAMP Salt

Ditoluyl-(L)-tartaric acid (200 g) was dissolved in 320 mL of reagent grade methanol. To the methanol then was added a stoichiometric amount of dl-3-DAMP (110.0 g) which titrated at 90% DAMP (10% toluene), and the solution warmed itself to 36°-40° C. and began to precipitate white solids. The batch was held and stirred at 40° C. for 31 hours. If run at room temperature, the yield of the correct diastereomeric salt continues to increase for about one month and levels off at about an 85% yield. After 8 days a 74-78% yield is expected. At 40° C., the 85-90% yield is obtained after about 31 hours. Higher temperatures increase the speed of interconversion, but at the cost of some decomposition.

The slurry was filtered at room temperature and carefully washed with 250 mL of room temperature methanol. The samples were air-dried overnight and weighed the following morning. Analysis of the salt produced is given below. Eighty-eight percent (263 g) of material which contained 99.2% 1-3-DAMP and 0.8% d-3-DAMP and had a specific rotation of -121.3° and a melting point of 148°-151.5° C. Some melting points showed softening at 130° C. This is believed to be residual toluene (from the dl-3-DAMP synthesis) on the crystals which was not removed in drying. It does not affect the use of the material.

EXAMPLE II

Conversion to free 1-3-DAMP and recovery of Ditoluyl-(L)-tartaric acid 1-3-DAMP Ditoluyl-(L)-tartaric acid salt (235.7 g) was slurried in 764 mL of deionized water. The slurry was chilled to less than 10° C. (If the free base is isolated above 10° C. one observes increasing amounts of racemization. In experiments with the dibenzoyl(d)tartaric acid salt, up to 2% inversion of the 1-DAMP was seen. Below 5° C. is preferable if possible.)

The pH then was adjusted using NH4OH. At a pH of 9, a solution was obtained. The pH was adjusted to 10.8 (adjusted for a temperature of 6°). This required about 260 mL of ammonium hydroxide.

The resulting oil was extracted twice with 250 mL aliquots of methylene chloride (poorer yields of 3-DAMP were obtained from hexane or t-butylmethyl ether extractions).

The methylene chloride extracts were combined and kept cold. The aqueous solution was set aside. The cold methylene chloride solution was washed with 147 mL of cold deionized water to remove residual salts and excess ammonia. The methylene chloride solution then was dried with 15 g MgSO4 (anhydrous), and methylene chloride was removed under vacuum to give 73.1 g of 1-3-DAMP as a 91% solution. The 1-3-DAMP was titrated in a 1:1 methanol water mixture against 0.1N HCl to determine this. (In some workups small amounts of hexanes or petroleum ether were used to wash the product into bottles or dropping funnels. This had no noticeable effect on the Grignard reaction. This material should be stable for several weeks without racemization at room temperature but is routinely stored as cold as possible. It is suitable for use in the Grignard reaction at this point.)

The aqueous solution which contains the ditoluyl-(L)-tartaric acid was treated with 837 mL of ethyl acetate. The pH was adjusted to 2.3-2.9 using concentrated HCl. As the pH goes through the 3-5 range a thick precipitate of the mono ammonium salt forms. Good stirring must be maintained to avoid formation of a solid mass. The free ditoluyl-(L)-tartaric acid goes into the ethyl acetate as it is formed. In experiments where the pH was allowed to go below 2.0, a small amount of ammonium hydroxide must be added to bring it back up as soon as possible or hydrolysis of the ditoluyl tartaric acid may occur. This mixture warms considerably during the HCl addition. A cool water bath helps maintain the mixture at close to room temperature.

The solvent layers were separated, and the water layer was washed with 180 mL of ethyl acetate. The ethyl acetate extracts were combined, and the water layer was discarded. The ethyl acetate solution was washed with 330 mL of deionized water to remove salts, and was dried using 33 g of MgSO4 (anhydrous). Ethyl acetate then was evaporated off under vacuum to leave a thick clear oil. This oil was taken up in 364 mL of methanol and an equivalent (116 g) of dl-3-DAMP was added. The 1-3-DAMP salt soon began to precipitate.

If the isolation of solid ditoluyl-(L)-tartaric acid is desired, 3 equivalents of isopropanol can be added. The ditoluyl-(L)-tartaric acid forms a crystalline diisopropanolate and the third equivalent keeps it mobile. This can be chilled and filtered to obtain about 70-80% of the material. A second crop can be obtained by evaporating it down. If the diisopropanolate is dried at 80° C., the isopropanol is removed. Alternatively, solid ditoluyl-(L)-tartaric can be obtained by pouring the thick oil onto a tray. Traces can be washed onto the tray with small amounts of acetone. If the oil is constantly stirred to break the surface, the solvents will evaporate and solids will form.

It can be seen that the present invention is significantly distinguishable from and superior to prior art methods for resolving 1-3-DAMP. The resolution purity is far superior in the present invention ranging from 96-100% enantiomeric excess (98-100% 1-3-DAMP by chiral liquid chromatography) in the salt.

No recycling or boil down is required to obtain 85-88% yield. The racemization occurs in situ, and the enantomerically pure 1-3-DAMP salt is precipitated (or d-3-DAMP depending upon which tartaric acid is used).

I claim:

1. A process for resolving 3-dimethylamino-2-methylpropiophenone (3-DAMP) material comprising:
   a) forming a methanol solution containing a mixture of both 1- and d-enantiomers of 3-DAMP;
   b) adding to said solution only one acid selected from the group consisting of ditoluyl-(L)-tartaric acid and ditoluyl-(D)-tartaric acid, so as to precipitate one of said enantiomers as a salt; and c) isolating the precipitate as a salt of a substantially pure enantiomer of 3-DAMP.

2. The process of claim 1 wherein said acid is ditoluyl-(L)-tartaric acid and said substantially pure enantiomer is 1-3-DAMP.

3. The process of claim 1 further including the step of recycling the methanol solution after isolation if said precipitate by further adding to the solution a mixture of both 1- and d-enantiomers of 3-DAMP and said one acid.

4. The process of claim 1 wherein, in step (b), an amount of said one acid equimolar to said mixture of 3-DAMP enantiomers is added to said solution.

5. The process of claim 1 further comprising having 3-DAMP material in said solution interconvert after step (b) so as to further precipitate said one of said enantiomers as a salt, and isolating said further precipitate.

6. The process of claim 5 further including the step of recycling the methanol solution after isolation of said precipitate by further adding to the solution a mixture of both 1- and d-enantiomers of 3-DAMP and said one acid.

7. The process of claim 5 further including the step of stirring said solution so as to facilitate interconversion of said 3-DAMP material.

8. The process of claim 5 wherein the interconversion occurs at a temperature of from about room temperature to about 40° C.

9. The process of claim 1 further comprising the step of converting the isolated precipitate to a free amine of said substantially pure enantiomer of 3-DAMP without substantial loss of optical purity.

10. The process of claim 9 wherein said acid is ditoluyl-(L)-tartaric acid and said substantially pure enantiomer is 1-3-DAMP.

11. The process of claim 10 wherein the isolated precipitate is converted to the free amine by forming an aqueous solution of said precipitate, and extracting 1-3-DAMP from said aqueous solution with an aprotic solvent.

12. The process of claim 11 wherein said aqueous solution is formed at a pH of about 9 or higher.

13. The process of claim 12 wherein said pH is within the range of from about 10.5 to about 11.

14. The process of claim 13 wherein said pH s about 10.8.

15. The process of claim 11 wherein the 1-3-DAMP is extracted from said aqueous solution at a temperature within the range of from about 0° C. to about 10° C.

16. The process of claim 15 wherein said temperature is between about 0° C. and about 5° C.

17. The process of claim 11 wherein said aprotic solvent is methylene chloride.

18. The process of claim 17 further including the step of separating said methylene chloride from said 1-3-DAMP.

* * * * *

UNITED STATES PATENT AND TRADEMARK OFFICE
CERTIFICATE OF CORRECTION

PATENT NO. : 5,227,526
DATED : July 13, 1993
INVENTOR(S) : John R. Duchek

It is certified that error appears in the above-indentified patent and that said Letters Patent is hereby corrected as shown below:

Col. 6, line 20, "s" should be --is--

Signed and Sealed this

Twenty-second Day of March, 1994

Attest:

BRUCE LEHMAN

Attesting Officer    Commissioner of Patents and Trademarks